US011458136B2

(12) United States Patent
Gendelman et al.

(10) Patent No.: US 11,458,136 B2
(45) Date of Patent: Oct. 4, 2022

(54) ANTIVIRAL PRODRUGS AND FORMULATIONS THEREOF

(71) Applicant: BOARD OF REGENTS OF THE UNIVERSITY OF NEBRASKA, Lincoln, NE (US)

(72) Inventors: Howard E. Gendelman, Omaha, NE (US); Benson Edagwa, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 54 days.

(21) Appl. No.: 16/981,325

(22) PCT Filed: Apr. 9, 2019

(86) PCT No.: PCT/US2019/026497
§ 371 (c)(1),
(2) Date: Sep. 16, 2020

(87) PCT Pub. No.: WO2019/199756
PCT Pub. Date: Oct. 17, 2019

(65) Prior Publication Data
US 2021/0113558 A1 Apr. 22, 2021

Related U.S. Application Data

(60) Provisional application No. 62/654,723, filed on Apr. 9, 2018.

(51) Int. Cl.
*C07D 239/00* (2006.01)
*A61K 31/44* (2006.01)
(Continued)

(52) U.S. Cl.
CPC .......... *A61K 31/505* (2013.01); *A61K 9/5146* (2013.01); *A61K 31/4439* (2013.01);
(Continued)

(58) Field of Classification Search
CPC ........ A61K 31/44; A61K 31/536; A61K 9/51; C07D 239/00; C07D 263/52; A61P 31/14; A61P 31/18
See application file for complete search history.

(56) References Cited

U.S. PATENT DOCUMENTS

| 5,145,684 A | 9/1992 | Liversidge et al. |
| 6,045,829 A | 4/2000 | Liversidge et al. |

(Continued)

FOREIGN PATENT DOCUMENTS

| EP | 0349242 A2 | 1/1990 |
| EP | 2682397 A1 | 1/2014 |

(Continued)

OTHER PUBLICATIONS

Namasivayam et al. "The journey of HIV-1 Non-nucleoside reverse transcriptase inhibitors (NNRTIs) from lab to clinic," J. Medicinal Chemistry, 2019, vol. 62, pp. 4851-4883 (Year: 2019).*

(Continued)

*Primary Examiner* — Shengjun Wang
(74) *Attorney, Agent, or Firm* — Goodwin Procter LLP

(57) ABSTRACT

The present invention provides prodrugs and methods of use thereof.

13 Claims, 8 Drawing Sheets

Figure 1:
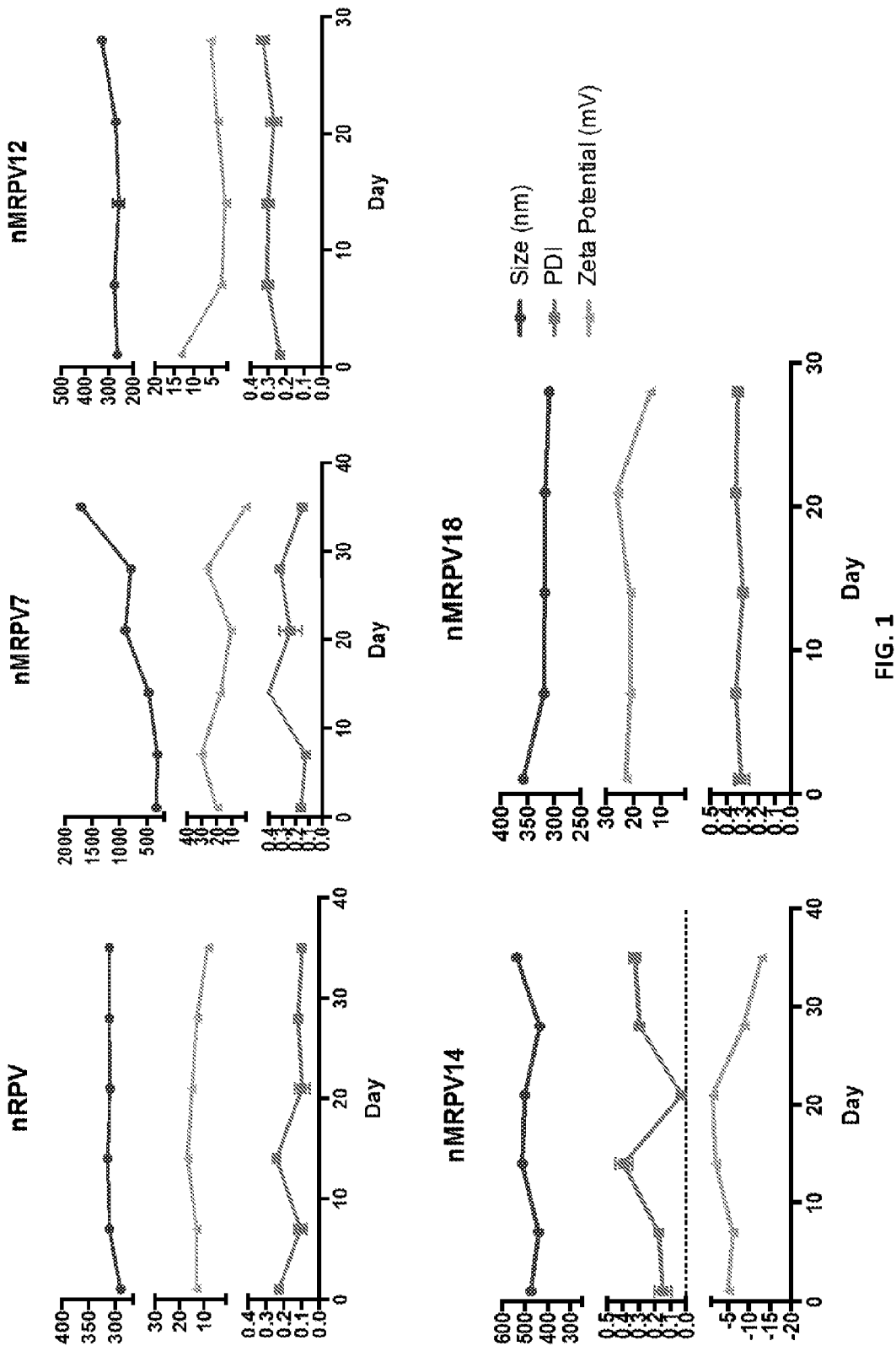

(51) Int. Cl.

| | | |
|---|---|---|
| *A61K 31/505* | (2006.01) | |
| *A61K 47/69* | (2017.01) | |
| *A61P 31/14* | (2006.01) | |
| *A61K 9/51* | (2006.01) | |
| *A61K 31/4439* | (2006.01) | |
| *A61K 31/496* | (2006.01) | |
| *A61K 31/536* | (2006.01) | |
| *A61K 31/551* | (2006.01) | |

(52) U.S. Cl.
CPC .......... *A61K 31/496* (2013.01); *A61K 31/536* (2013.01); *A61K 31/551* (2013.01); *A61K 47/6935* (2017.08); *A61P 31/14* (2018.01)

(56) References Cited

U.S. PATENT DOCUMENTS

| | | | |
|---|---|---|---|
| 6,068,858 | A | 5/2000 | Liversidge et al. |
| 6,835,396 | B2 | 12/2004 | Brynjelsen et al. |
| 7,112,340 | B2 | 9/2006 | Kipp et al. |
| 9,808,428 | B2 | 11/2017 | Gendelman et al. |
| 2002/0041898 | A1 | 4/2002 | Unger et al. |
| 2004/0138157 | A1 | 7/2004 | Walker |
| 2005/0048002 | A1 | 3/2005 | Rabinow et al. |
| 2006/0280430 | A1 | 12/2006 | Rabinow et al. |
| 2007/0003608 | A1 | 1/2007 | Almond et al. |
| 2007/0042988 | A1 | 2/2007 | Klumpp et al. |
| 2008/0241256 | A1 | 10/2008 | Kuhn |
| 2009/0274765 | A1 | 11/2009 | Beduneau et al. |
| 2011/0039798 | A1 | 2/2011 | Doncel et al. |
| 2011/0085987 | A1 | 4/2011 | Wang et al. |
| 2012/0202823 | A1* | 8/2012 | Zeidan .................... A61P 37/08 514/252.11 |
| 2013/0236553 | A1 | 9/2013 | Gendelman et al. |
| 2013/0244966 | A1 | 9/2013 | Milne et al. |
| 2014/0017330 | A1 | 1/2014 | Vinogradov |
| 2014/0099283 | A1 | 4/2014 | Gosselin et al. |
| 2014/0323425 | A1 | 10/2014 | Calvez et al. |
| 2015/0297587 | A1* | 10/2015 | Gelbard ................ A61K 31/427 424/490 |
| 2017/0304308 | A1 | 10/2017 | Gendelman et al. |

FOREIGN PATENT DOCUMENTS

| | | |
|---|---|---|
| JP | H04295420 A | 10/1992 |
| WO | WO-9902665 A1 | 1/1999 |
| WO | WO-2000066090 A1 | 11/2000 |
| WO | WO-02087424 A2 | 11/2002 |
| WO | WO-2004069812 A1 | 8/2004 |
| WO | WO-2005072706 A2 | 8/2005 |
| WO | WO-2006116764 A1 | 11/2006 |
| WO | WO-2007095269 A2 | 8/2007 |
| WO | WO-2009051837 A2 | 4/2009 |
| WO | WO-2010009075 A1 | 1/2010 |
| WO | WO-2010011814 A1 | 1/2010 |
| WO | WO-2011119566 A1 | 9/2011 |
| WO | WO-2012037320 A2 | 3/2012 |
| WO | WO-2012061480 A2 | 5/2012 |
| WO | WO-20120158811 A2 | 11/2012 |
| WO | WO-2013158549 A1 | 10/2013 |
| WO | WO-2014085795 A1 | 6/2014 |
| WO | WO-2014169207 A1 | 10/2014 |
| WO | WO-2015108945 A2 | 7/2015 |
| WO | WO-2015127437 A1 | 8/2015 |
| WO | WO-2016057866 A1 | 4/2016 |
| WO | WO-2016099982 A2 | 6/2016 |
| WO | WO-20170223280 A2 | 12/2017 |
| WO | WO-20190140365 A1 | 7/2019 |
| WO | WO-2019199756 A1 | 10/2019 |

OTHER PUBLICATIONS

Agarwal, A.G., et al., Synthesis and biological evaluation of fatty acyl ester derivatives of (−)-2',3'-dideoxy-3'-thiacytidine, J Med Chem, 55(10): 4861-4871 (2012).

Arainga, M., et al., Opposing regulation of endolysosomal pathways by long-acting nanoformulated antiretroviral therapy and HIV-1 in human macrophages, Retrovirology, 12: 5 (2015).

Baert, L., et al., Development of a long-acting injectable formulation with nanoparticles of rilpivirine (TMC278) for HIV treatment, Eur J Pharm Biopharm, 72(3): 502-508 (2009).

Balkundi, S., et al., Comparative manufacture and cell-based delivery of antiretroviral nanoformulations, Int J Nanomedicine, 6: 3393-3404 (2011).

Batrakova, E.V., et al., Cell-mediated drugs delivery, Expert Opin Drug Deliv, 8(4): 415-433 (2011).

Bhatia, M., et al., Nanoparticle technology for the delivery of poorly water-soluble drug, Pharm Tech, 30(2): 82-92 (2006).

Chattopadhyay, N., et al., Solid lipid nanoparticles enhance the delivery of the HIV protease inhibitor, atazanavir, by a human brain endothelial cell line, Pharm Res, 25(10): 2262-2271 (2008).

Dobrowska-Mas, E., Insights on fatty acids in lipophlic prodrug strategy, IRJPAC, 14(4): 1-10 (2017).

Edagwa, B.J., et al., Development of HIV reservoir targeted long acting nanoformulated antiretroviral therapies, Curr Med Chem, 21(36): 4186-4198 (2014).

Edagwa, B.J., et al., Long-acting antituberculous therapeutic nanoparticles target macrophage endosomes, FASEB J, 28(12): 5071-5082 (2014).

Gautam, N., et al., Pharmacokinetics, biodistribution, and toxicity of folic acid-coated antiretroviral nanoformulations, Antimicrob Agents Chemother, 58(12): 7510-7519 (2014).

Gautam, N., et al., Preclinical pharmacokinetics and tissue distribution of long-acting nanoformulated antiretroviral therapy, Antimicrob Agents Chemother, 57(7): 3110-3120 (2013).

Gavegnano, C., et al., Antiretroviral therapy in macrophages: implication for HIV eradication. Antivir Chem Chemother, 20(2): 63-78 (2009).

Guarino, V.R., et al., Prodrugs of amides, imides and other NH-acidic compounds in Prodrugs: Challenges and Rewards Part 1, p. 24, American Association of Pharmaceutical Sciences, New York, pp. 134-187 (2007).

Guo, D., et al., Creation of a long-acting nanoformulated 2',3'-dideoxy-3'-thiacytidine, J Acquir Immune Defic Syndr, 74(3): e75-e83 (2017).

Guo, D., et al., Endosomal trafficking of nanoformulated antiretroviral therapy facilitates drug particle carriage and HIV clearance, J Virol, 88(17): 9504-9513 (2014).

Huang, B., et al., First discovery of a potential carbonate prodrug of NNRTI drug candidate RDEA427 with submicromolar inhibitory activity against HIV-1 K103N/Y181C double mutant strain, Bioorg Med Chem Lett, 28(8): 1348-1351 (2018).

Irby, D., et al., Lipid-drug conjugate for enhancing drug delivery, Mol Pharm, 14(5): 1325-1338 (2017).

Jain, S.K., et al., Mannosylated gelatin nanoparticles bearing an anti-HIV drug didanosine for site-specific delivery, Nanomedicine, 4(1): 41-48 (2008).

Kanmogne, G.D., et al., Mononuclear phagocyte intercellular crosstalk facilitates transmission of cell-targeted nanoformulated atiretroviral drugs to human brain endothelial cells, Int J Nanomedicine, 7: 2373-2388 (2012).

Kinman, L., et al., Optimization of lipid-indinavir complexes for localization in lymphoid tissues of HIV-infected macaques, J Acquir Immune Defic Sundr, 42(2): 155-161 (2006).

Krise, J.P., et al., Prodrugs of Amines in Prodrugs: Challenges and Rewards Part 1, American Association of Pharmaceutical Sciences, New York, pp. 102-131 (2007).

Law, D., et al., Physicochemical considerations in the preparation of amorphous ritonavir-poly(ethylene glycol) 8000 solid dispersions, J Pharm Sci, 90(8): 1015-1025 (2001).

Li, Q., et al., Synthesis of lamivudine stearate and antiviral activity of stearic acid-g-chitosan oligosaccharide polymeric micelles delivery system, Eur J Pharm Sci, 41(3-4): 498-507 (2010).

Lin, Z., et al., ProTide generated long-acting abacavir nanoformulations, Chem Commun (Cambridge), 54(60): 8371-8374 (2018).

(56) References Cited

OTHER PUBLICATIONS

Liu, F., et al., Targeted cancer therapy with novel high drug-loading nanocrystals, J Pharm Sci, 99(8): 3542-3551 (2010).
Low, P.S., et al., Discovery and development of folic-acid-based receptor targeting for imaging and therapy of cancer and inflammatory diseases, Acc Chem Res, 41(1): 120-129 (2008).
McGuigan, C., et al., The application of phosphoramidate ProTide technology to the potent anti-HCV compound 4'-azidocytidine (R1479), Bioorg Med Chem Lett, 19(15): 4250-4254 (2009).
Moghimi, S.M., et al., Poloxamers and poloxamines in nanoparticle engineering and experimental medicine, Trends Biotechnol, 18(10): 412-420 (2000).
Nowacek, A.S., Development of a macrophage-mediated delivery system for crystalline antiretroviral nanoparticles, Dissertation, University of Nebraska, 219 pages (2011).
Nowacek, A.S., et al., NanoART synthesis, characterization, uptake, release and toxicology for human monocyte-macrophage drug delivery, Nanomedicine (Lond.), 4(8): 903-917 (2009).
Nowacek, A.S., et al., Nanoformulated antiretroviral Combinations extend drug release and antiretroviral responses in HIV-1 infected macrophages: Implications for neuroAIDS therapeutics, J Neuroimmune Pharmacol, 5(4): 592-601 (2010).
PCT/US2015/054826 International Search Report and Written Opinion dated Jan. 7, 2016.
PCT/US2019/013462 International Search Report and Written Opinion dated Mar. 5, 2019.
PCT/US2019/026497 International Search Report and Written Opinion dated Jun. 18, 2019.
Puligujja, P., et al., Macrophage Folate Receptor-Targeted Antiretroviral Therapy Facilitates Drug Entry, Retention, Antiretroviral Activities and Biodistribution for Reduction of Human Immunodeficiency Virus Infections, Nanomedicine, 9(8): 1263-1273 (2013).
Puligujja, P., et al., Pharmacodynamics of long-acting folic acid-receptor targeted ritonavir-boosted atazanavir nanoformulations, Biomaterials, 41: 141-150 (2015).
Rohde, M., et al., Biological conversion of aripiprazole lauroxil—An N-acyloxymethyl aripiprazole prodrug, Results Pharma Sci, 4: 19-25 (2014).
Rowe, R.C., et al., Handbook of Pharmaceutical Excipients, 6th Edition, Pharmaceutical Press, pp. 317-324 (2009).
The essential chemical industry—online, pp. 1-8, (2013) retrieved on Feb. 8, 2018 from <http://www.essentialchemical industry.ord/materials-and-applications/surfactants.html>.
The Merck Index Online entries for "Atazanavir" (monograph M2119), "Idinavir" (monograph M6253), and "Ritonavir" (monograph M9636), 5 pages (2013).
Thomas, T.P., et al., Folate-targeted nanoparticles show efficacy in the treatment of inflammatory arthritis, Arthritis Rheum, 63(9): 2671-2680 (2011).
Xia, W., et al., A functional folate receptor is induced during macrophage activation and can be used to target drugs to activated macrophages, Blood, 113(2): 438-446 (2009).
U.S. Appl. No. 15/517,581, filed Apr. 7, 2017, Allowed.
U.S. Appl. No. 16/772,995, filed Jun. 15, 2020, Pending.

* cited by examiner

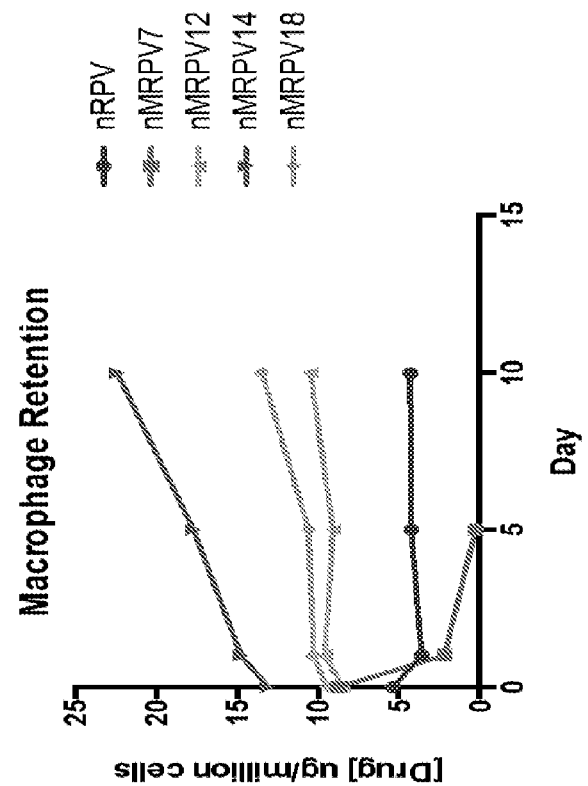
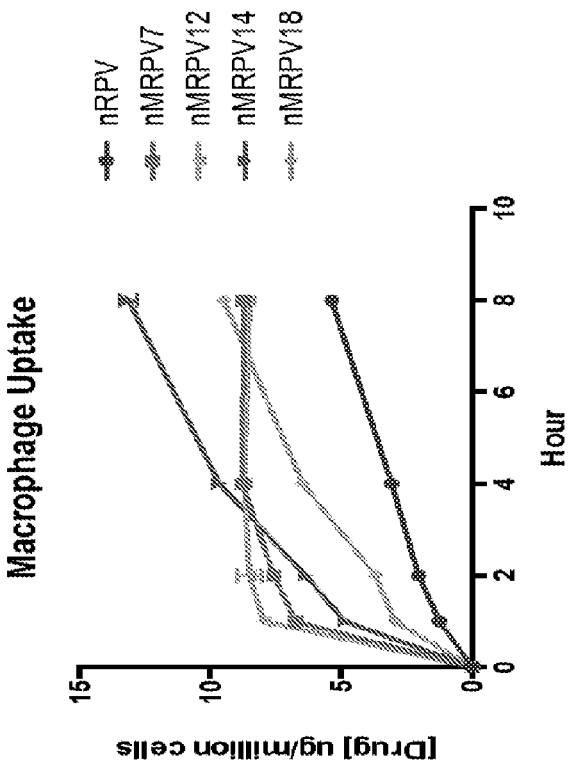
FIG. 2A
FIG. 2B

ANTIVIRAL PRODRUGS AND FORMULATIONS THEREOF

This application is a § 371 application of PCT/US2019/026497, filed Apr. 9, 2019, which claims priority under 35 U.S.C. § 119(e) to U.S. Provisional Patent Application No. 62/654,723, filed Apr. 9, 2018. The foregoing applications are incorporated by reference herein.

This invention was made with government support under Grants Nos. P01DA028555, R01AG043540, R01NS034239, R01NS036126, P01MH064570, P01NS031492, P30AI078498, R24OD018546, and P30MH062261 awarded by the National Institutes of Health. The government has certain rights in the invention.

FIELD OF THE INVENTION

The present invention relates generally to the delivery of therapeutics. More specifically, the present invention relates to compositions and methods for the delivery of therapeutic agents to a patient for the treatment of a disease or disorder.

BACKGROUND OF THE INVENTION

Rilpivirine is an FDA approved non-nucleoside reverse transcriptase inhibitor (NNRTI) with potent activity and a unique resistance profile for the treatment of HIV-1 infection (Sharma et al., J. Antimicrob. Chemother. (2012) 68:250-256; Baert et al., Eur. J. Pharm. Biopharm. (2009) 72:502-508). Further, the combination of RPV and the integrase inhibitor dolutegravir (DTG) has demonstrated similar effectiveness compared to the leading three- or four-drug combination antiretroviral treatments (Libre et al., Conference on Retroviruses and Opportunistic Infections (2017) Seattle, Wash., Abstract 44LB). Despite its effectiveness, drug limitations include regimen adherence, bioavailability, absorption, viral reservoir penetrance, and failure to reduce viral loads present at greater than 100,000 copies/mL (Imaz, et al., AIDS Rev. (2012) 14:268-278). These limitations underscore the need for more potent compounds and improved formulation and drug delivery strategies (Edagwa, et al., Expert Opin. Drug Deliv. (2017) 14:1281-1291). Studies have revealed preference for long acting injectable ART amongst HIV-1 infected patients; with 73% of those surveyed indicating that they would consider long acting formulations (Williams, et al., Nanomedicine (2013) 8(11): 1807-1813). This number goes up to 84% when patients were asked about monthly dosing, opposed to weekly or biweekly dosing. Conceivably, bimonthly or longer dosing intervals would be even more attractive. Accordingly, there is a need for long acting formulations of NNRTIs.

SUMMARY OF THE INVENTION

In accordance with the instant invention, prodrugs of a non-nucleoside reverse transcriptase inhibitor are provided. In a particular embodiment, the prodrug comprises an ester comprising an aliphatic or alkyl group (e.g., an aliphatic or alkyl comprising about 3 to about 30 carbons). In a particular embodiment, the aliphatic or alkyl group is the alkyl chain of a fatty acid or a C4-C24 unsaturated or saturated alkyl or aliphatic group, optionally substituted with at least one heteroatom. In a particular embodiment, the non-nucleoside reverse transcriptase inhibitor selected from the group consisting of rilpivirine, nevirapine, efavirenz, delavirdine, etravirine, and doravirine. Composition comprising at least one prodrug of the instant invention and at least one pharmaceutically acceptable carrier are also encompassed by the present invention.

In accordance with another aspect of the instant invention, nanoparticles comprising at least one prodrug of the instant invention and at least one polymer or surfactant are provided. In a particular embodiment, the prodrug is crystalline. In a particular embodiment, the polymer or surfactant is an amphiphilic block copolymer such as an amphiphilic block copolymer comprising at least one block of poly(oxyethylene) and at least one block of poly(oxypropylene) (e.g., poloxamer 407). The nanoparticle may comprise a polymer or surfactant linked to at least one targeting ligand. An individual nanoparticle may comprise targeted and non-targeted surfactants. In a particular embodiment, the nanoparticles have a diameter of about 100 nm to 1 µm. Composition comprising at least one nanoparticle of the instant invention and at least one pharmaceutically acceptable carrier are also encompassed by the present invention.

In accordance with another aspect of the instant invention, methods for treating, inhibiting, and/or preventing a disease or disorder in a subject in need thereof are provided. The methods comprise administering to the subject at least one prodrug or nanoparticle of the instant invention, optionally within a composition comprising a pharmaceutically acceptable carrier. In a particular embodiment, the disease or disorder is cancer, viral infection, or a clotting disorder. In a particular embodiment, the viral infection is an HIV, hepatitis B, hepatitis C, influenza A, influenza B, herpes simplex, or Ebola infection. In a particular embodiment, the method further comprises administering at least one further therapeutic agent or therapy for the disease or disorder, e.g., at least one additional anti-HIV compound.

BRIEF DESCRIPTIONS OF THE DRAWING

FIG. 1 provides graphs showing the stability of nRPV and nMRPV (nMRPV7, nMRPV12, nMRPV14, and nMRPV18) nanoformulations at 25° C. over the indicated periods of time. Each graph provides particle size (nm), polydispersity index, and zeta potential (mV) as determined by dynamic light scattering (DLS).

Figure 2C:
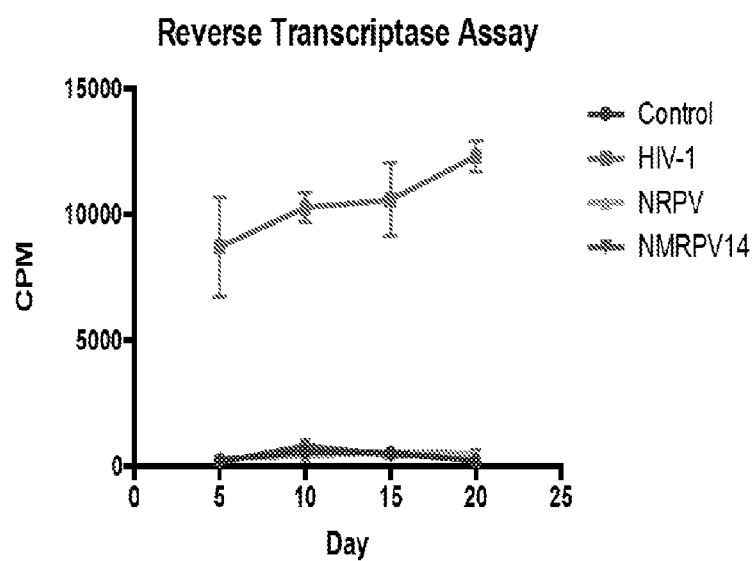
Figure 2D:
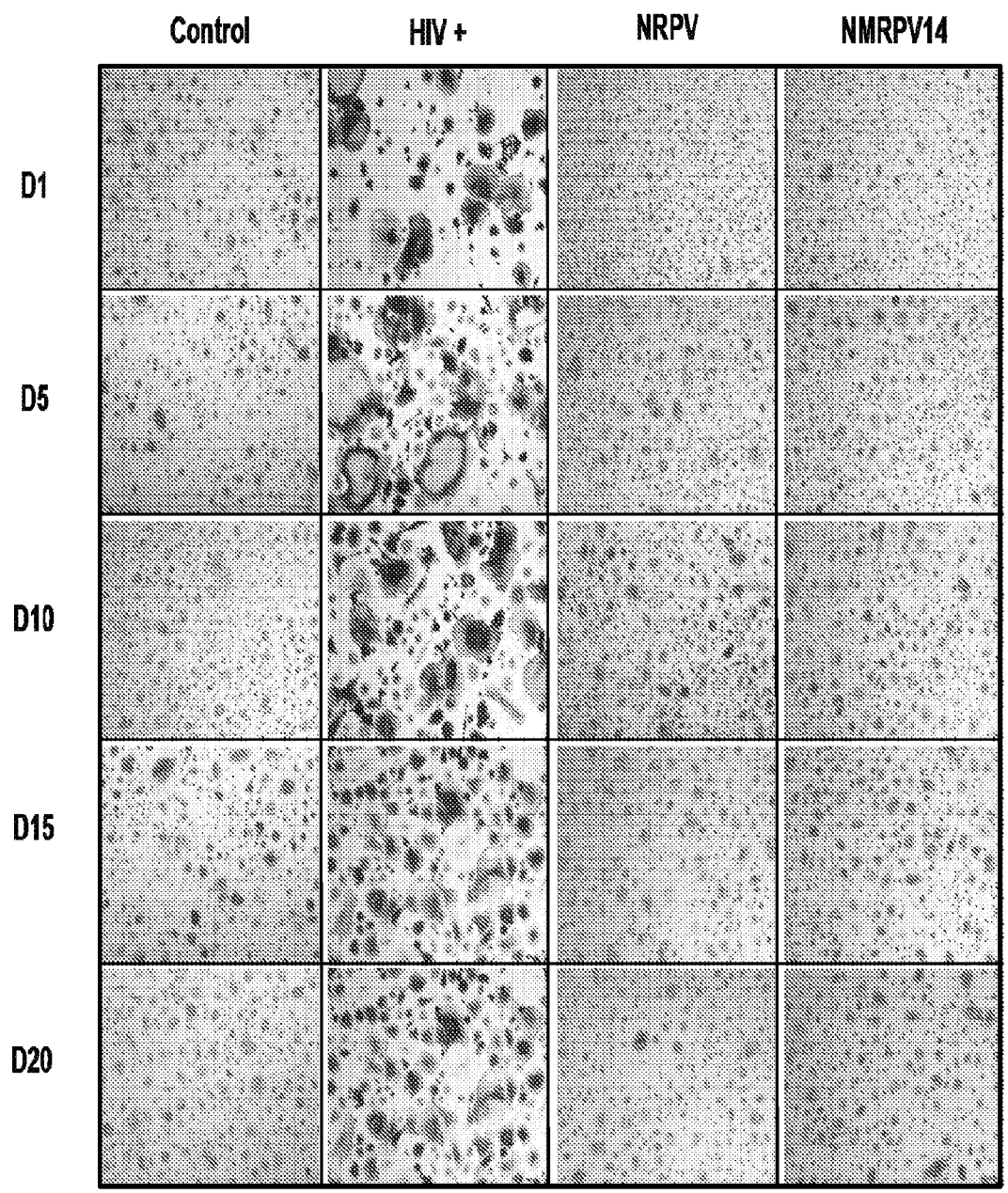

FIG. 2A provides a graph of the drug uptake as measured by UPLC-UV/Vis by human monocyte derived macrophages (MDM) treated at a dose of 30 µM for 8 hours. FIG. 2B provides a graph of drug retention by MDM treated at a dose of 30 µM for 8 hours and then collected at day 1, 5, and 10 for intracellular drug analysis. FIG. 2C provides a graph of HIV-1 reverse transcriptase activity in MDM treated with 100 µM drug for 8 hours and challenged with HIV-ADA for 16 hours on days 1, 5, 10, 15, or 20 post treatment. FIG. 2D provides images of p24 stained MDM cells at 10 days post-challenge.

Figure 3A:
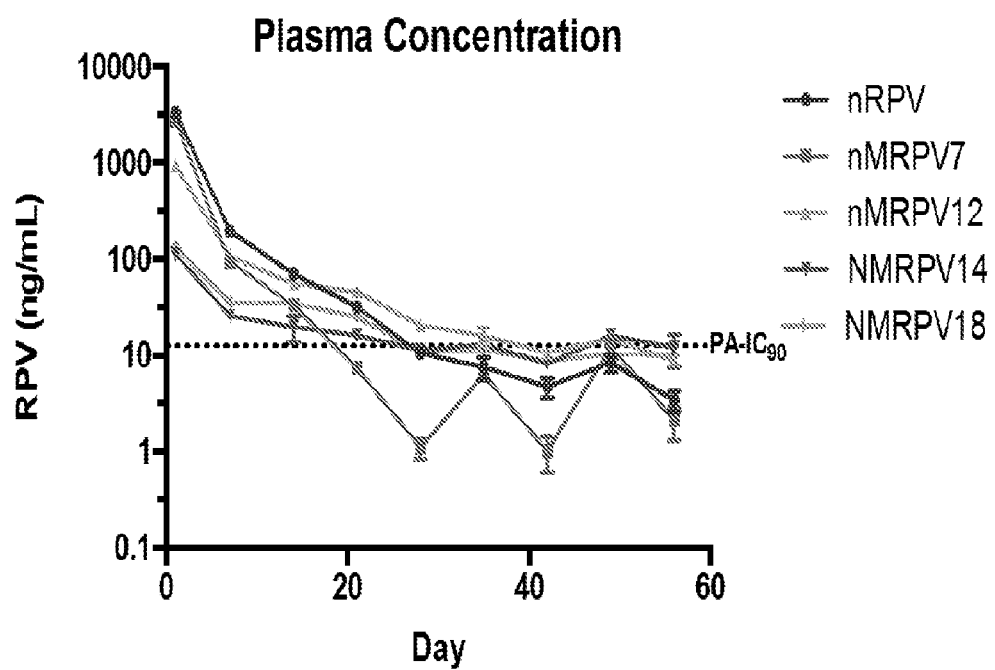
Figure 3B:
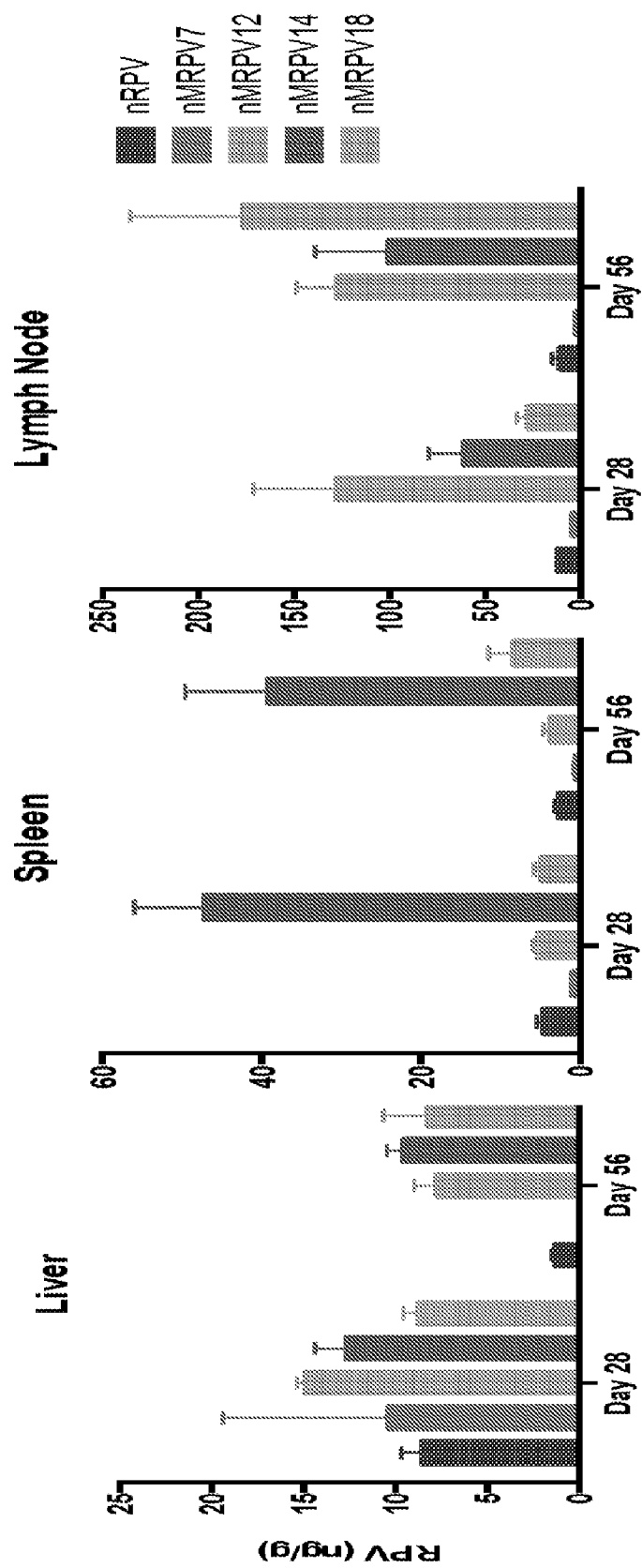

FIG. 3A provides a graph of the plasma drug levels in Balb/c mice administered an intramuscular (IM) dose of 45 mg/kg RPV-equivalents on Day 0. Plasma was collected weekly over a 56 day period and RPV concentrations were measured by UPLC-MS/MS. FIG. 3B provides a graph of the tissue drug levels in the Balb/c mice. Liver, spleen, and lymph nodes were collected at day 28 and 56 and subsequently analyzed for RPV concentrations by UPLC-MS/MS.

Figure 4A:
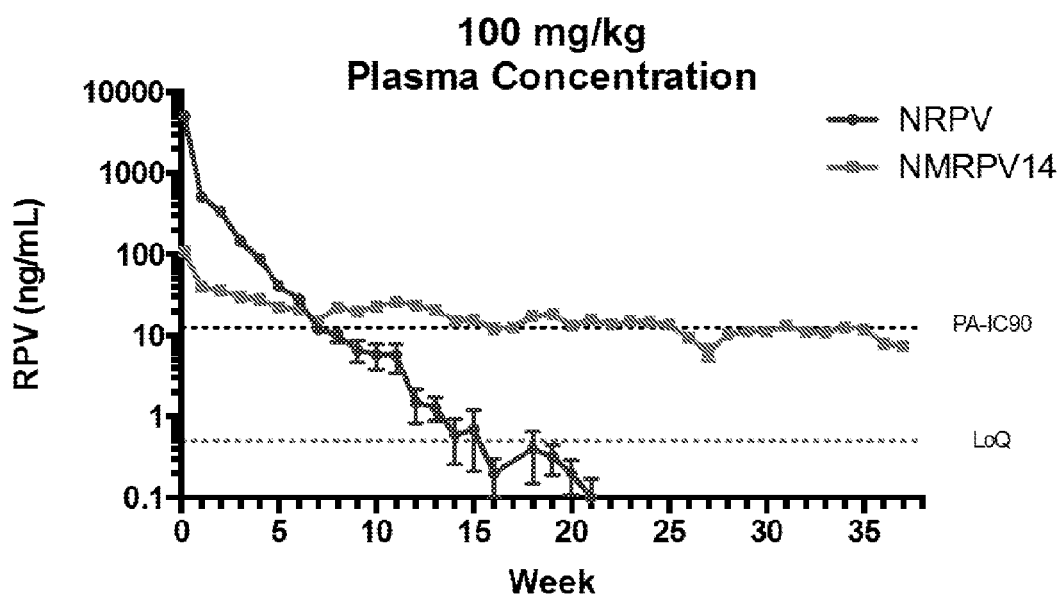
Figure 4B:
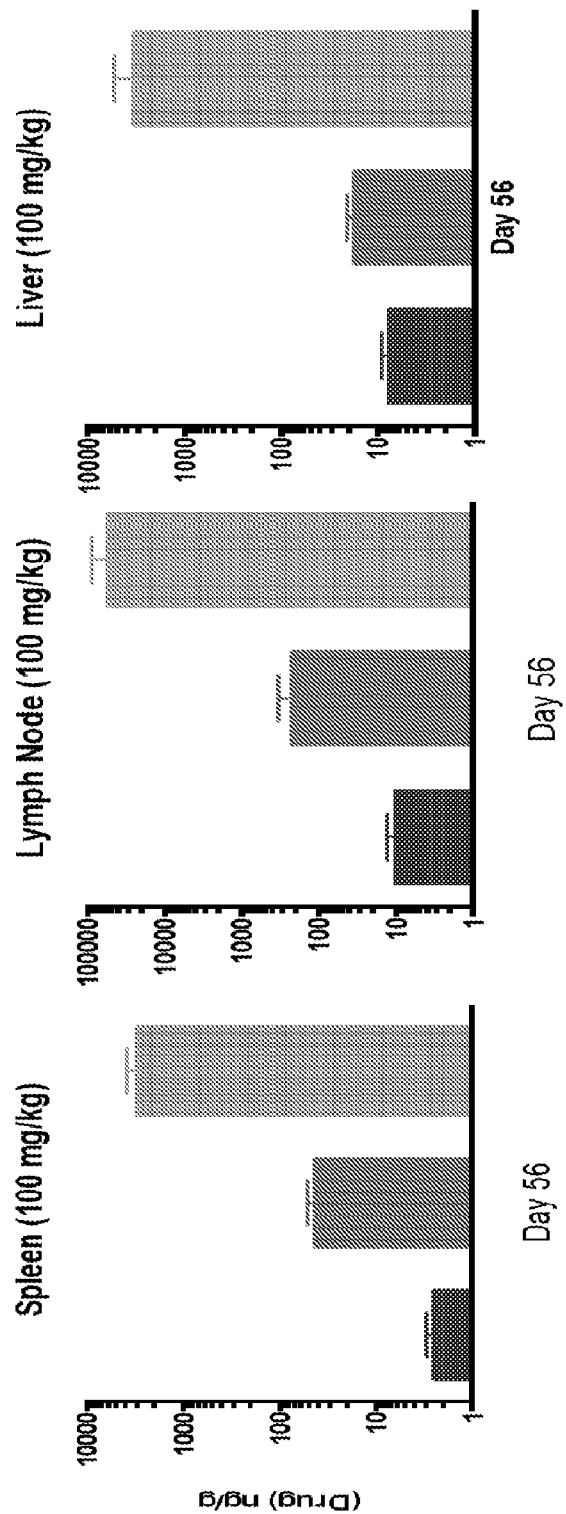

FIG. 4A provides a graph of the plasma drug levels in Balb/c mice administered an intramuscular (IM) dose of 100 mg/kg RPV-equivalents on Day 0. Plasma was collected weekly over a 37 week period and RPV concentrations were measured by UPLC-MS/MS. FIG. 4B provides a graph of the tissue drug levels in the Balb/c mice. Liver, spleen, and lymph nodes were collected at day 56 and subsequently analyzed for RPV concentrations by UPLC-MS/MS. Left and middle columns are nanoformulations of RPV and the right column is nMPRV14.

DETAILED DESCRIPTION OF THE INVENTION

Long acting slow effective release ART (LASER ART) formulations can extend dosing intervals, reduce systemic toxicity, and improve pharmacokinetic (PK) and pharmacodynamic (PD) profiles (Sillman, et al., Nat. Commun. (2018) 9:443; Zhou, et al., Biomaterials (2018) 151:53-65; McMillan, et al., Antimicrob. Agents Chemother. (2018) 62:e01316-17). Herein, novel cell and tissue targeted NNRTI prodrugs, long acting, slow effective release formulations thereof, and methods of synthesis and use thereof are provided. NNRTI prodrugs (e.g., prodrugs of rilpivirine (RPV), nevirapine (NVP), efavirenz (EFV), delavirdine (DLV), etravirine (ETR), and doravirine (MK-1439)) of the instant invention comprise hemiaminal ester moieties. For example, the NNRTI may have the nitrogens of the NNRTI masked by conjugates to form reversible hemiaminal esters. The hydrophobic and lipophilic prodrugs and their slow effective release formulations exhibit enhanced potency and efficacy, increased cellular and tissue penetration and extended half-lives compared to parent NNRTI. The prodrugs and their formulations of the instant invention and their combinations can be used in the management of viral and other microbial infections.

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination therapies, e.g., antiretroviral therapies (ART), which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-lives. Furthermore, failure can also be attributed, in part, to limited drug access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR) has been used as pre-exposure prophylaxis and post-exposure prophylaxis.

The prodrugs and nanoformulated prodrugs (nanoparticles) provided herein extend the apparent drug half-life, increase hydrophobicity and lipophilicity, improved protein binding capacity and antiretroviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as anti-HIV agents, the prodrugs and nanoformulations of the instant invention are also effective against other viral infections including, without limitation: hepatitis B virus (HBV), hepatitis C virus (HCV), herpes simplex virus (HSV), and Ebola virus. The prodrugs and nanoformulations of the instant invention are also effective against other microbial infections such as *Mycobacterium tuberculosis*. The prodrugs and nanoformulations of the instant invention are also effective against cancer and platelet disorders.

The present invention describes novel, potent, broad spectrum prodrugs with improved biological activity over parent drugs. Methods for the encapsulation of the prodrugs into long acting slow effective formulations for efficient intracellular and tissue delivery and extended drug half-lives are also provided. The long acting slow effective release (LASER) compositions described herein exhibit enhanced potency and may be used as effective therapeutic or preventative interventions against cancer and microbial infections (e.g., viral infections).

Prodrugs of the instant invention allow for the efficient intracellular delivery of non-nucleoside reverse transcriptase inhibitors (NNRTIs). Herein, prodrugs which are derivatives of NNRTI wherein nitrogen (e.g., —NH—, or —$NH_2$) are masked by hydrophobic and lipophilic cleavable moieties (e.g., therapeutic fatty alcohols) are utilized. In a particular embodiment, the nitrogen is masked with hydroxymethyl linkers to form reversible hemiaminal esters. The hydrophobic and lipophilic cleavable moiety (e.g., therapeutic fatty alcohols) exhibit antiviral activity against enveloped viruses (Katz, et al., Ann. NY Acad. Sci. (1994) 724:472-88). Synergistic interactions between therapeutic fatty alcohols and nucleoside analogs substantially enhance antiviral potency of the nucleosides (Marcelletti, et al., Antiviral Res. (2002) 56:153-66).

As described herein, the prodrugs may comprise labile therapeutic fatty alcohols to improve drug potency, accelerate intracellular and tissue penetrance, protein binding, and bioavailability. The hydrophobic nature of the synthesized prodrugs facilitates encapsulation into long acting slow release drug nanocrystals with improved biopharmaceutical features. The nanoformulations of the instant invention may be composed of prodrug particles dispersed in sterile aqueous suspensions and stabilized by polymeric excipients, lipids, and/or surfactants or polymers. Without being bound by theory, the mechanism of drug release involves dissolution of the prodrug from the nanoparticle followed by efficient cleavage to generate two bioactive agents, i.e., the NNRTI (e.g., to inhibit reverse transcriptase) and broad-spectrum antiviral fatty alcohols.

The benefits of the system described herein include, without limitation, improved drug potency, bioavailability and extended half-life for patient convenience. Indeed, the nanoformulations described in this invention displayed significant increase in drug uptake by monocyte-derived macrophages (MDM). Also, the modified drug and nanoparticles exhibited enhanced potency through increased and extended inhibition of viral replication. Therefore, the nanoformulations of the instant invention allow for enhancement of antiviral potency and accelerated drug delivery to anatomical reservoirs of infection.

In accordance with the instant invention, prodrugs of NNRTI are provided. In a particular embodiment, the prodrug comprises a NNRTI wherein a nitrogen (e.g., a primary or secondary amine) is conjugated to an optionally substituted aliphatic or alkyl group. In a particular embodiment, a methyl ester is attached to a nitrogen of the NNRTI. In a particular embodiment, the prodrug comprises a hemiaminal ester.

In a particular embodiment, the NNRTI is selected from the group consisting of:

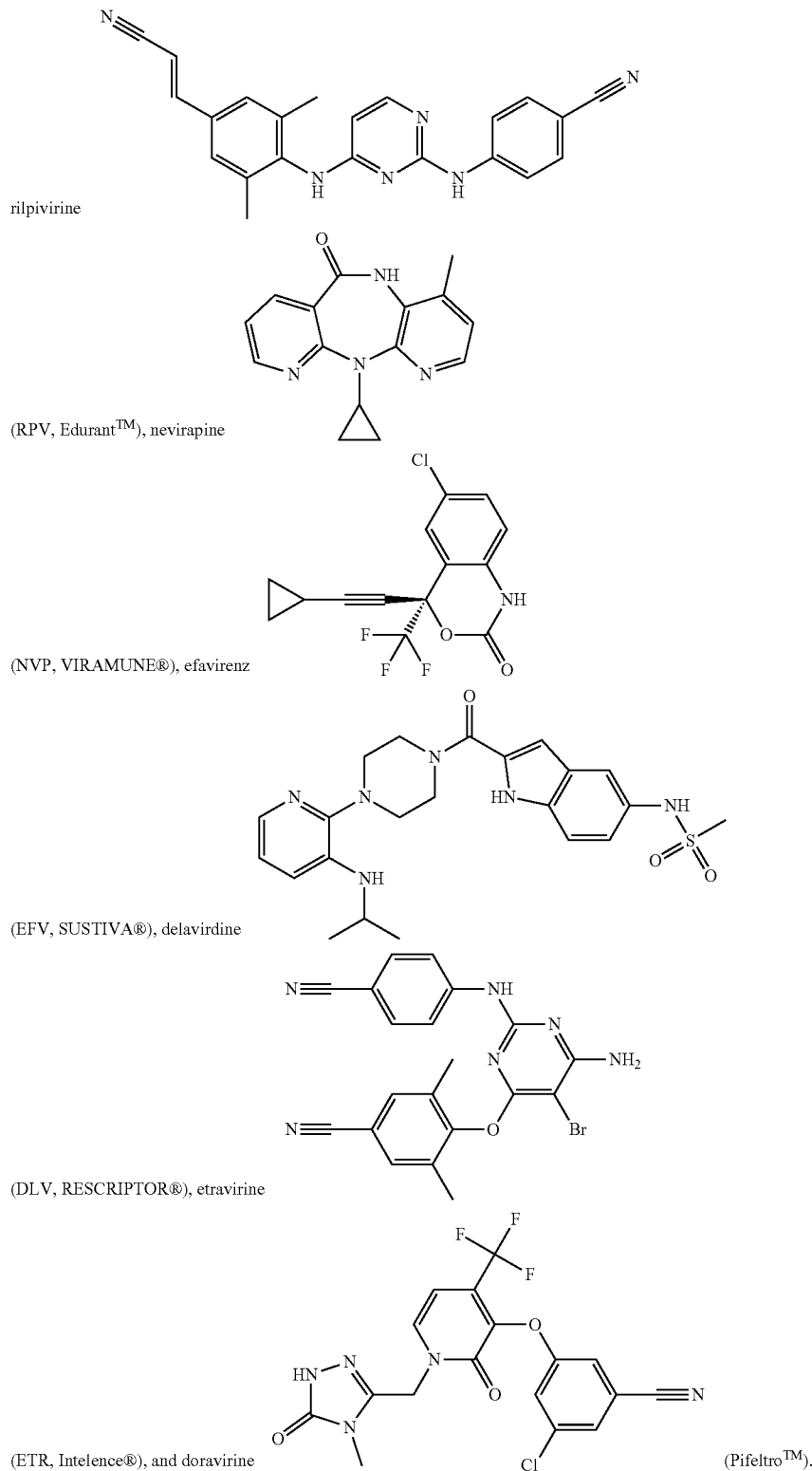

rilpivirine (RPV, Edurant™), nevirapine (NVP, VIRAMUNE®), efavirenz (EFV, SUSTIVA®), delavirdine (DLV, RESCRIPTOR®), etravirine (ETR, Intelence®), and doravirine (Pifeltro™).

The prodrug of the instant invention may be selected from one of Formulas (I)-(III) or a pharmaceutically acceptable salt thereof:

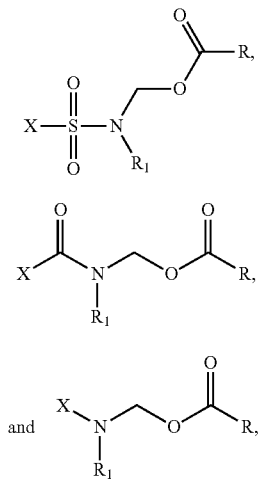

wherein:

X is a NNRTI; $R_1$ is H or an optionally substituted alkyl, aryl, or cycloalkyl; and R is an optionally substituted aliphatic or alkyl. In a particular embodiment, the nitrogen and $R_1$ group are part of the NNRTI, along with the depicted intervening atoms. For example, $R_1$ may complete an alkyl, aryl, or cycloalkyl within the NNRTI.

With regard to R, the aliphatic or alkyl group may be unsaturated or saturated, and may be substituted with at least one heteroatom (e.g., O, N, or S). In a particular embodiment, the alkyl or aliphatic group is hydrophobic. In a particular embodiment, the alkyl or aliphatic group comprises about 3 to about 30 carbons (e.g., in the main chain of the alkyl or aliphatic group), which may be substituted with at least one heteroatom (e.g., O, N, or S). In a particular embodiment, R is a C4-C24 unsaturated or saturated alkyl or aliphatic group, which may be substituted with at least one heteroatom (e.g., O, N, or S). In a particular embodiment, R is a C4-C20 unsaturated or saturated alkyl or aliphatic group, which may be substituted with at least one heteroatom (e.g., O, N, or S). In a particular embodiment, R is a C6-C18 unsaturated or saturated alkyl or aliphatic group, which may be substituted with at least one heteroatom (e.g., O, N, or S). In a particular embodiment, R is the alkyl chain of a fatty acid (saturated or unsaturated), particularly a C4-C24 fatty acid, a C4-C20 fatty acid, or a C6-C18 fatty acid.

In a particular embodiment, the prodrug of the instant invention is an NNRTI wherein a hydrogen of a primary amine or secondary amine has been replaced with

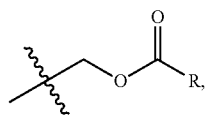

wherein R is an optionally substituted aliphatic or alkyl, and pharmaceutically acceptable salts thereof. The aliphatic or alkyl group may be unsaturated or saturated, and may be substituted with at least one heteroatom (e.g., O, N, or S). In a particular embodiment, the alkyl or aliphatic group is hydrophobic. In a particular embodiment, the alkyl or aliphatic group comprises about 3 to about carbons (e.g., in the main chain of the alkyl or aliphatic group), which may be substituted with at least one heteroatom (e.g., O, N, or S). In a particular embodiment, R is a C4-C24 unsaturated or saturated alkyl or aliphatic group, which may be substituted with at least one heteroatom (e.g., O, N, or S). In a particular embodiment, R is a C4-C20 unsaturated or saturated alkyl or aliphatic group, which may be substituted with at least one heteroatom (e.g., O, N, or S). In a particular embodiment, R is a C6-C18 unsaturated or saturated alkyl or aliphatic group, which may be substituted with at least one heteroatom (e.g., O, N, or S). In a particular embodiment, R is the alkyl chain of a fatty acid (saturated or unsaturated), particularly a C4-C24 fatty acid, a C4-C20 fatty acid, or a C6-C18 fatty acid.

In a particular embodiment, the prodrug of the instant invention is selected from:

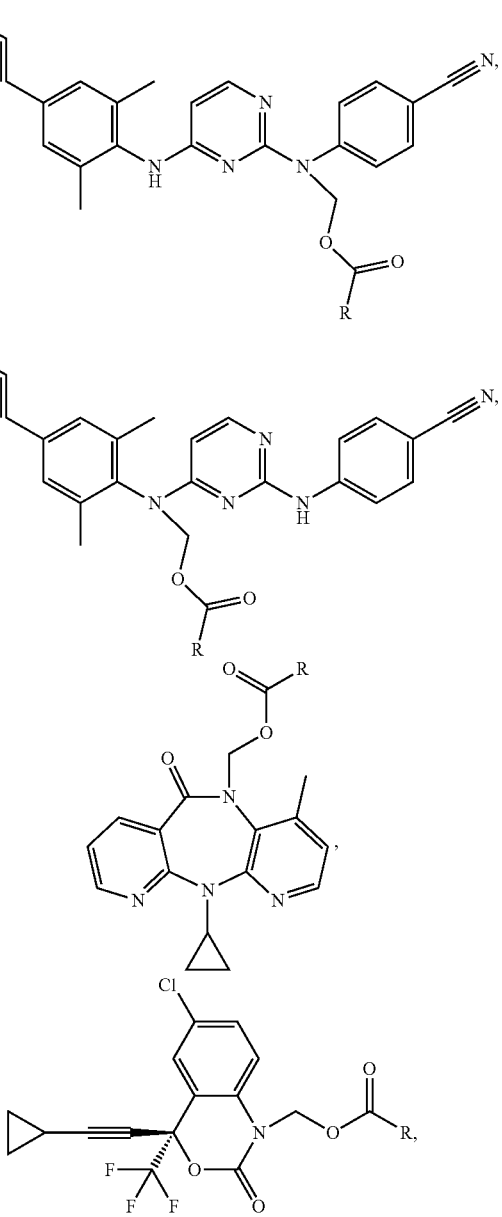

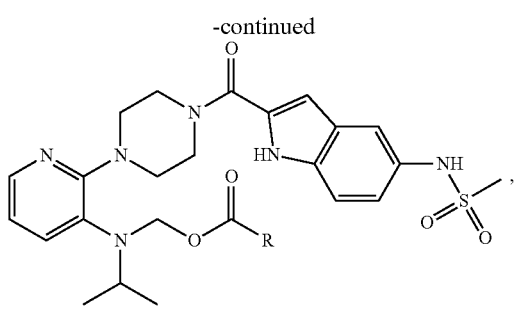

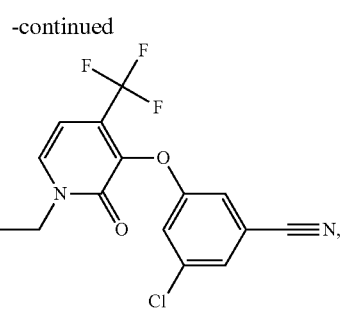

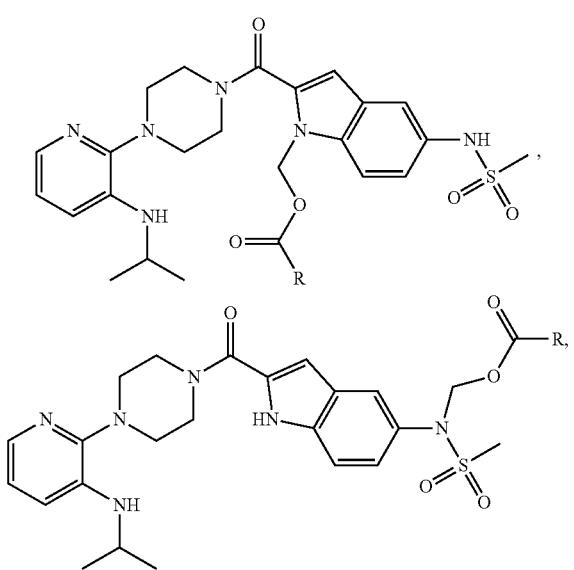

wherein R is an optionally substituted aliphatic or alkyl, and pharmaceutically acceptable salts thereof. The aliphatic or alkyl group may be unsaturated or saturated, and may be substituted with at least one heteroatom (e.g., O, N, or S). In a particular embodiment, the alkyl or aliphatic group is hydrophobic. In a particular embodiment, the alkyl or aliphatic group comprises about 3 to about 30 carbons (e.g., in the main chain of the alkyl or aliphatic group), which may be substituted with at least one heteroatom (e.g., O, N, or S). In a particular embodiment, R is a C4-C24 unsaturated or saturated alkyl or aliphatic group, which may be substituted with at least one heteroatom (e.g., O, N, or S). In a particular embodiment, R is a C4-C20 unsaturated or saturated alkyl or aliphatic group, which may be substituted with at least one heteroatom (e.g., O, N, or S). In a particular embodiment, R is a C6-C18 unsaturated or saturated alkyl or aliphatic group, which may be substituted with at least one heteroatom (e.g., O, N, or S). In a particular embodiment, R is the alkyl chain of a fatty acid (saturated or unsaturated), particularly a C4-C24 fatty acid, a C4-C20 fatty acid, or a C6-C18 fatty acid.

In a particular embodiment, the prodrug of the instant invention is selected from:

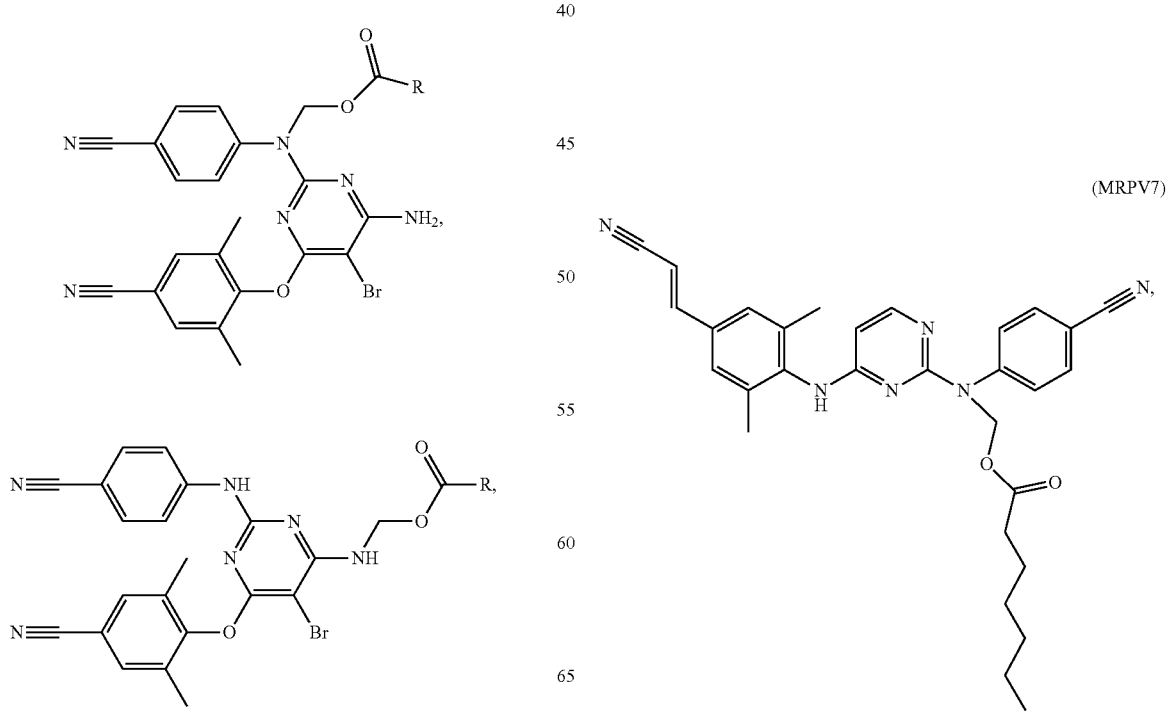

(MRPV12)

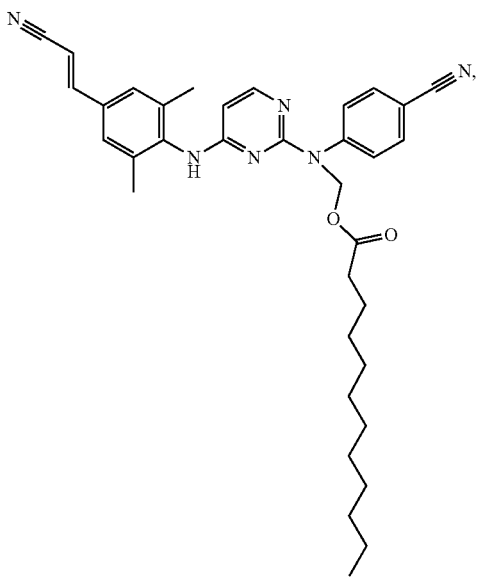

(MRPV18)

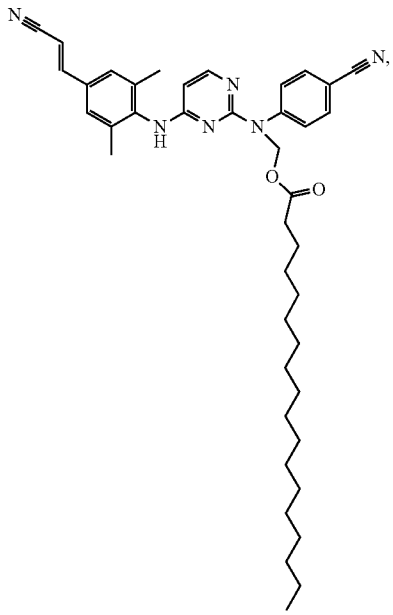

and pharmaceutically acceptable salts thereof. In a particular embodiment, the prodrug is MRPV14 or a pharmaceutically acceptable salt thereof.

The instant invention also encompasses nanoparticles (sometimes referred to herein as nanoformulations) comprising the prodrug of the instant invention. The nanoparticles may be used for the delivery of the compounds to a cell or host (e.g., in vitro or in vivo). In a particular embodiment, the nanoparticle is used for the delivery of antiretroviral therapy to a subject. The nanoparticles of the instant invention comprise at least one prodrug and at least one surfactant or polymer. In a particular embodiment, the nanoparticles comprise a spectroscopic-defined surfactant/polymer:drug ratio that maintains optimal targeting of the drug nanoparticle to maintain a macrophage depot. These components of the nanoparticle, along with other optional components, are described hereinbelow.

Methods of synthesizing the nanoparticles of the instant invention are known in the art. In a particular embodiment, the methods generate nanoparticles comprising a prodrug (e.g., crystalline or amorphous) coated (either partially or completely) with a polymer and/or surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the polymers or surfactants are firstly chemically modified with targeting ligands and then used directly or mixed with non-targeted polymers or surfactants in certain molar ratios to coat on the surface of prodrug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or (MRPV14)

without further purification, although the avoidance of further purification is desirable for quicker production of the nanoparticles. In a particular embodiment, the nanoparticles are synthesized using milling and/or homogenization. Targeted nanoparticles (e.g., using ligands with high molecular weight) may be developed through either physically or chemically coating and/or binding on the surface of polymers or surfactants and/or drug nanosuspensions.

In a particular embodiment, the nanoparticles of the instant invention are synthesized by adding the prodrug (e.g., crystals) to a polymer or surfactant solution and then generating the nanoparticles (e.g., by wet milling or high pressure homogenization). The prodrug and polymer or surfactant solution may be agitated prior the wet milling or high pressure homogenization.

The nanoparticles of the instant invention may be used to deliver at least one prodrug of the instant invention to a cell or a subject (including non-human animals). The nanoparticles of the instant invention may further comprise at least one other agent or compound, particularly a bioactive agent, particularly a therapeutic agent (e.g., antiviral compound) or diagnostic agent, particularly at least one antiviral or antiretroviral. In a particular embodiment, the nanoparticles of the instant invention comprise at least two therapeutic agents, particularly wherein at least one is a prodrug of the instant invention. For example, the nanoparticle may comprise a NNRTI prodrug of the instant invention and at least one other therapeutic agent (e.g., an anti-HIV agent).

In a particular embodiment, the nanoparticles of the instant invention are a submicron colloidal dispersion of nanosized prodrug crystals stabilized by polymers or surfactants (e.g., surfactant-coated drug crystals; a nanoformulation). In a particular embodiment, the prodrug may be crystalline (solids having the characteristics of crystals), amorphous, or are solid-state nanoparticles of the prodrug that is formed as crystal that combines the drug and polymer or surfactant. In a particular embodiment, the prodrug is crystalline. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the prodrug and, optionally, the hydrophobic portion of the surfactant are crystalline.

In a particular embodiment, the nanoparticle of the instant invention is up to about 2 or 3 μm in diameter (e.g., z-average diameter) or its longest dimension, particularly up to about 1 μm (e.g., about 100 nm to about 1 μm). For example, the diameter or longest dimension of the nanoparticle may be about 50 to about 800 nm. In a particular embodiment, the diameter or longest dimension of the nanoparticle is about 50 to about 750 nm, about 50 to about 500 nm, about 200 nm to about 500 nm, or about 200 nm to about 400 nm. The nanoparticles may be, for example, rod shaped, elongated rods, irregular, or round shaped. The nanoparticles of the instant invention may be neutral or charged. The nanoparticles may be charged positively or negatively.

As stated hereinabove, the nanoparticles of the instant invention comprise at least one polymer or surfactant. A "surfactant" refers to a surface-active agent, including substances commonly referred to as wetting agents, detergents, dispersing agents, or emulsifying agents. Surfactants are usually organic compounds that are amphiphilic.

Examples of polymers or surfactants include, without limitation, synthetic or natural phospholipids, PEGylated lipids (e.g., PEGylated phospholipid), lipid derivatives, polysorbates, amphiphilic copolymers, amphiphilic block copolymers, poly(ethylene glycol)-co-poly(lactide-co-glycolide) (PEG-PLGA), their derivatives, ligand-conjugated derivatives and combinations thereof other polymers or surfactants and their combinations that can form stable nanosuspensions and/or can chemically/physically bind to the targeting ligands of HIV infectable/infected CD4+ T cells, macrophages and dendritic cells can be used in the instant invention. Further examples of polymers or surfactants include, without limitation: 1) nonionic surfactants (e.g., pegylated and/or polysaccharide-conjugated polyesters and other hydrophobic polymeric blocks such as poly (lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1, 2-distearoyl-sn-glecro-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide) (PNIPAM), and poly (allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof).

The polymer or surfactant of the instant invention may be charged or neutral. In a particular embodiment, the polymer or surfactant is neutral or negatively charged (e.g., poloxamers, polysorbates, phospholipids, and their derivatives).

In a particular embodiment, the polymer or surfactant is an amphiphilic block copolymer or lipid derivative. In a particular embodiment, at least one polymer or surfactant of the nanoparticle is an amphiphilic block copolymer, particularly a copolymer comprising at least one block of poly (oxyethylene) and at least one block of poly(oxypropylene). In a particular embodiment, the polymer or surfactant is a triblock amphiphilic block copolymer. In a particular embodiment, the polymer or surfactant is a triblock amphiphilic block copolymer comprising a central hydrophobic block of polypropylene glycol flanked by two hydrophilic blocks of polyethylene glycol. In a particular embodiment, the surfactant is poloxamer 407.

In a particular embodiment, the amphiphilic block copolymer is a copolymer comprising at least one block of poly(oxyethylene) and at least one block of poly(oxypropylene). In a particular embodiment, the amphiphilic block copolymer is a poloxamer. Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. In a particular embodiment, the poloxamer is poloxamer 407 (Pluronic® F127).

In a particular embodiment of the invention, the polymer or surfactant is present in the nanoparticle and/or solution to synthesize the nanoparticle (as described herein) at a concentration ranging from about 0.0001% to about 10% or 15% by weight. In a particular embodiment, the concentration of the polymer or surfactant ranges from about 0.01% to about 15%, about 0.01% to about 10%, about 0.1% to about 10%, or about 0.1% to about 6% by weight. In a particular embodiment, the nanoparticle comprises at least about 50%, 75%, 80%, 85%, 90%, 95%, 97%, 98%, 99% or higher therapeutic agent (prodrug) by weight. In a particular embodiment, the nanoparticles comprise a defined drug:polymer/surfactant ratio. In a particular embodiment, the drug:polymer/surfactant ratio (e.g., by weight) is from about 10:6 to about 1000:6, about 20:6 to about 500:6, about 50:6 to about 200:6, or about 100:6.

As stated hereinabove, the polymer or surfactant of the instant invention may be linked to a targeting ligand. The targeting of the nanoparticles (e.g., to macrophage) can provide for superior targeting, decreased excretion rates, decreased toxicity, and prolonged half-life compared to free drug or non-targeted nanoparticles. A targeting ligand is a compound that specifically binds to a specific type of tissue or cell type (e.g., in a desired target:cell ratio). For example, a targeting ligand may be used for engagement or binding of a target cell (e.g., a macrophage) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand may be linked directly to the polymer or surfactant or via a linker. Generally, the linker is a chemical moiety comprising a covalent bond or a chain of atoms that covalently attaches the ligand to the polymer or surfactant. The linker can be linked to any synthetically feasible position of the ligand and the polymer or surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either or both ends of the polymer or surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted polymers or surfactants. In a particular embodiment, the molar ratio of targeted and non-targeted polymers or surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted polymers or surfactants. In a particular embodiment, the nanoparticles/nanoformulations of the instant invention comprise a folate targeted polymer or surfactant and a non-targeted version of the polymer or surfactant. In a particular embodiment, the nanoparticles/nanoformulations of the instant invention comprise folate-poloxamer 407 (FA-P407) and/or poloxamer 407.

Examples of targeting ligands include but are not limited to macrophage targeting ligands, CD4+ T cell targeting ligands, dendritic cell targeting ligands, and tumor targeting ligands. In a particular embodiment, the targeting ligand is a macrophage targeting ligand. The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands include, without limitation, hyaluronic acid, gp120 and peptide fragments thereof, and ligands or antibodies specific for CD4, CCR5, CXCR4, CD7, CD111, CD204, CD49a, CD29, CD19, CD20, CD22, CD171, CD33, Leis-Y, WT-1, ROR1, MUC16, MUC1, MUC4, estrogen receptor, transferrin receptors, EGF receptors (e.g. HER2), folate receptor, VEGF receptor, FGF receptor, androgen receptor, NGR, Integrins, and GD2. In a particular embodiment, the targeting ligand is folic acid.

As stated hereinabove, the nanoparticles of the instant invention may comprise a further therapeutic agent. The instant invention also encompasses therapeutic methods wherein the prodrug and/or nanoparticles of the instant invention are co-administered with another therapeutic agent. In a particular embodiment, the therapeutic agent is hydrophobic, a water insoluble compound, or a poorly water soluble compound, particularly when included in the nanoparticle. For example, the therapeutic agent may have a solubility of less than about 10 mg/ml, less than 1 mg/ml, more particularly less than about 100 µg/ml, and more particularly less than about 25 µg/ml in water or aqueous media in a pH range of 0-14, preferably between pH 4 and 10, particularly at 20° C.

In a particular embodiment, the therapeutic agent is an antiviral or an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). In a particular embodiment, the therapeutic agent is an anti-HIV agent. An anti-HIV compound or an anti-HIV agent is a compound which inhibits HIV (e.g., inhibits HIV replication and/or infection). Examples of anti-HIV agents include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse transcriptase. NRTIs comprise a sugar and base. Examples of nucleoside-analog reverse transcriptase inhibitors include, without limitation, adefovir dipivoxil, adefovir, lamivudine, telbivudine, entecavir, tenofovir, stavudine, abacavir, didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), rilpivirne (TMC278, Edurant™), DAPY (TMC120), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors. Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, GSK1265744 (cabotegravir), GSK1349572 (dolutegravir), GS-9883 (bictegravir), and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX® B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not NNRTIs may be combined with the NNRTI prodrugs of the instant invention. In a particular embodiment, the anti-HIV therapy is highly active antiretroviral therapy (HAART).

The instant invention encompasses compositions (e.g., pharmaceutical compositions) comprising at least one prodrug and/or nanoparticle of the instant invention and at least one pharmaceutically acceptable carrier. As stated hereinabove, the nanoparticle may comprise more than one therapeutic agent. In a particular embodiment, the pharmaceutical composition comprises a first nanoparticle comprising a first prodrug and a second nanoparticle comprising a second prodrug, wherein the first and second prodrugs are different. The compositions (e.g., pharmaceutical compositions) of the instant invention may further comprise other therapeutic agents (e.g., other anti-HIV compounds (e.g., those described herein)).

The present invention also encompasses methods for preventing, inhibiting, and/or treating a disease or disorder. The methods comprise administering a prodrug and/or nanoparticle of the instant invention (optionally in a composition) to a subject in need thereof. In a particular embodiment, the disease or disorder is a microbial (e.g., viral) infection, cancer, or a blood clotting disorder (e.g., the prodrug or nanoparticle of the invention can be used as an antiplatelet drug to inhibit or prevent formation of a blood clot). Microbial infections include, without limitation, viral, bacterial, fungal, mycobacyterial and parasitic infections. In a particular embodiment, the disease or disorder is a viral infection. Examples of viral infections include, without limitation: HIV, Hepatitis B, Hepatitis C, Influenza A, Influenza B, Ebola, and Herpes Simplex, including co-infections such as HIC and hepatitis B or HIV and hepatitis C. In a particular embodiment, the viral infection is a retroviral or lentiviral infection, particularly an HIV infection (e.g., HIV-1). In a particular embodiment, the cancer includes, but is not limited to, leukemia (e.g., acute lymphoblastic leukemia, acute myeloid leukemia, chronic lymphocytic leukemia, chronic myelogenous leukemia), lymphoma (e.g., Hodgkin lymphoma, Non-Hodgkin lymphoma), multiple myeloma, breast cancer, prostate cancer, pancreatic cancer, colon cancer, thyroid cancer, bladder cancer, liver cancer, neuroblastoma, brain cancers (e.g., gliomas, meningiomas, and pituitary adenomas), lung cancer, ovarian cancer, stomach cancer, skin cancer (e.g., melanoma), cervical cancer, testicular cancer, kidney cancer, carcinoid tumors, and bone cancer.

The prodrugs and/or nanoparticles of the instant invention (optionally in a composition) can be administered to an animal, in particular a mammal, more particularly a human, in order to treat/inhibit/prevent the disease or disorder (e.g., an HIV infection). The pharmaceutical compositions of the instant invention may also comprise at least one other therapeutic agent such as an antiviral agent, particularly at least one other anti-HIV compound/agent. The additional anti-HIV compound may also be administered in a separate pharmaceutical composition from the prodrugs or compositions of the instant invention. The pharmaceutical compositions may be administered at the same time or at different times (e.g., sequentially).

The dosage ranges for the administration of the prodrugs, nanoparticles, and/or compositions of the invention are those large enough to produce the desired effect (e.g., curing, relieving, treating, and/or preventing the disease or disorder (e.g., HIV infection), the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than about 5 µg/kg, greater than about 50 µg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The prodrugs and nanoparticles described herein will generally be administered to a patient as a pharmaceutical composition. The term "patient" as used herein refers to human or animal subjects. These prodrugs and nanoparticles may be employed therapeutically, under the guidance of a physician.

The pharmaceutical compositions comprising the prodrugs and/or nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the prodrugs and/or nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of prodrugs and/or nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the prodrug and/or nanoparticle dispersed in a medium that is compatible with the site of injection.

Prodrugs and/or nanoparticles of the instant invention may be administered by any method. For example, the prodrugs and/or nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the prodrug and/or nanoparticle is parenterally. In a particular embodiment, the prodrug and/or nanoparticle is administered orally, intramuscularly, subcutaneously, or to the bloodstream (e.g., intravenously). Pharmaceutical compositions for injection are known in the art. If injection is selected as a method for administering the prodrug and/or nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a prodrug and/or nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the prodrugs and/or nanoparticles of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months. In a particular embodiment, the prodrugs and/or nanoparticles of the instant invention are administered less than once every two months.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "prodrug" refers to a compound that is metabolized or otherwise converted to a biologically active or more active compound or drug, typically after administration. A prodrug, relative to the drug, is modified chemically in a manner that renders it, relative to the drug, less active, essentially inactive, or inactive. However, the chemical modification is such that the corresponding drug is generated by metabolic or other biological processes, typically after the prodrug is administered.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., CCl$_3$ or CF$_3$), alkoxyl, alkylthio, hydroxy, methoxy, carboxyl, oxo, epoxy, alkyloxycarbonyl, alkylcarbonyloxy, amino, carbamoyl (e.g., NH$_2$C(=O)— or NHRC(=O)—, wherein R is an alkyl), urea (—NHCONH$_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred.

The following examples provide illustrative methods of practicing the instant invention and are not intended to limit the scope of the invention in any way.

Example 1

Synthesis of MRPV

Derivatization of RPV with iodomethyl esters was performed as depicted:

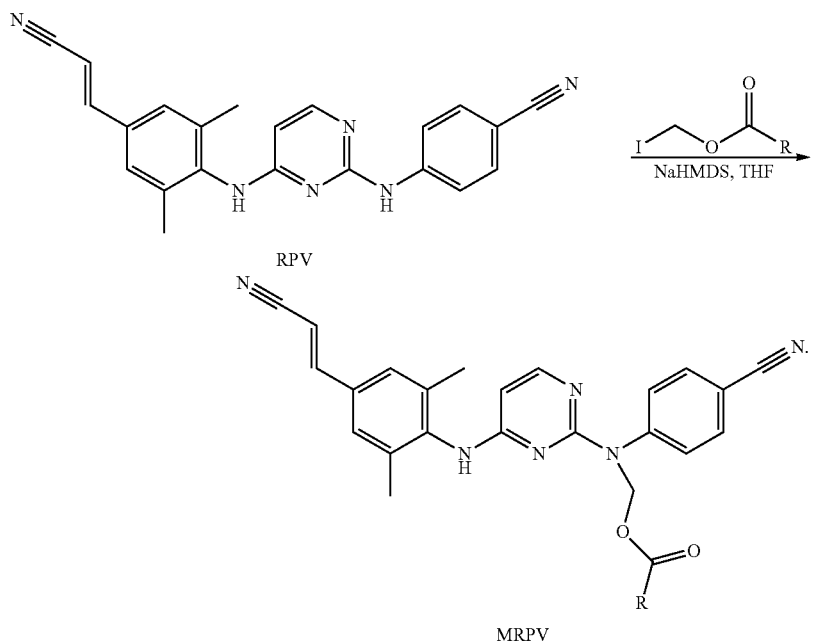

RPV (1 mol) was dried by azeotroping from anhydrous pyridine and then suspended in anhydrous THE and cooled to −80° C. under argon. Sodium bis(trimethylsilyl) amide (NaHMDS) (2 mol, 1.0 M solution in THF) was added to the mixture and stirring was continued for 10 minutes. Iodomethyl esters (1.2 mol, solution in THF) was added drop-wise to the deprotonated parent compound and the mixture was stirred for 48 hours at room temperature. The reaction mixture was then cooled to 0° C. and quenched with aqueous saturated ammonium chloride solution. The solvent was removed under vacuum, and the desired prodrugs were isolated on a silica column chromatography. The purified MRPV prodrugs were characterized using mass spectrometry, high performance liquid chromatography (HPLC), Fourier-transform infrared spectroscopy (FTIR), and nuclear magnetic resonance (NMR) spectroscopy.

MRPV prodrugs with R groups comprising varying carbon chain lengths were synthesized. Specifically, MRPV7, MRPV12, MRPV14, and MPRV18 were synthesized. The $^1$H-NMR spectrum of MRPV7, MRPV12, MRPV14, and MPRV18 showed the presence of an intense broad peak at 1.21-1.49 ppm and other peaks corresponding to the aliphatic protons on the fatty acid moiety. FTIR spectra also showed peaks corresponding to alkane ($CH_2$—$CH_2$) stretching of the fatty acid alkyl derivatizing promoieties in the MRPV prodrugs, but not the parent drug RPV.

Formulation Synthesis

RPV nanocrystals (nRPV) and MRPV nanocrystals (nMRPV7, nMRPV12, nMRPV14 and nMRPV18) were coated with either cell or tissue receptor targeted or nontargeted poloxamer 407 (P407), poloxamer 338 (P338), 1,2-distearoyl-sn-glycero-3-phosphocholine (DSPC), 1,2-distearoyl-sn-glycero-3-phosphoethanolamine-N-[carboxy (polyethylene glycol)-2000 (DSPE-PEG) or polyvinyl alcohol (PVA). The nanocrystals may also be stabilized with polysorbate and polyethylene glycol surfactants. A drug to surfactant ratio of 10:1 by weight was used to manufacture MRPV nanoparticles. Briefly, 1-5% (w/v) MRPV and 0.5-2.5% (w/v) P407 were mixed in sterile phosphate buffer or 10 mM HEPES buffer, pH 7.8. The premixed suspensions were nanoformulated by wet milling or high-pressure homogenization at 20,000-psi until desirable size and polydispersity index were achieved. The nRPV and nMRPV nanoformulations were characterized for particle size, polydispersity index (PDI) and zeta potential by dynamic light scattering (DLS) (FIG. 1). This was done on a Malvern Zetasizer, Nano Series Nano-ZS (Malvern Instruments Inc, Westborough, Mass.). Ultra-performance liquid chromatography-tandem mass spectrometer (UPLC-MS/MS) was used for drug quantitation.

Macrophage Uptake and Retention

Human monocytes were obtained by leukapheresis from HIV-1/2 and hepatitis B seronegative donors and then purified by counter-current centrifugal elutriation (Balkundi et al., Intl. J. Nanomed. (2011) 6:3393-3404; Nowacek et al., Nanomed. (2009) 4(8):903-917). Human monocytes were plated in a 12-well plate at a density of $1.0 \times 10^6$ cells per well using DMEM supplemented with 10% heat-inactivated pooled human serum, 1% glutamine, 10 µg/mL ciprofloxacin, and 50 µg/mL gentamicin. Cells were maintained at 37° C. in a 5% $CO_2$ incubator. After 7 days of differentiation in the presence of 1000 U/mL recombinant human macrophage colony stimulating factor (MCSF), MDM were treated with 30 µM nRPV, nMRPV7, nMRPV12, nMRPV14 or nMRPV18. Uptake of drug was assessed by measurements of intracellular drug concentrations at 1, 2, 4 and 8 hours after treatment. For drug retention studies, cells were treated for 8 hours then washed with PBS and maintained with half-media changes every other day until collection at days 1, 5 and 10. For both studies, adherent MDM were washed with PBS, then scraped into PBS, and counted at indicated time points using a Countess™ automated cell counter (Invitrogen, Carlsbad, Calif.). Cells were pelleted by centrifugation at 3,000 rpm for 8 minutes at 4° C. Cell pellets were briefly sonicated in 200 µL methanol to extract drug and centrifuged at 14,000 rpm for 10 minutes at 4° C. to pellet cell debris. Drug content was determined by UPLC-ultraviolet/visible (UV/Vis).

Antiretroviral Activities

Antiretroviral efficacy was determined by measurements of HIV reverse transcriptase (RT) activity. To assess antiretroviral efficacy, MDM were treated with 100 µM nRPV or nMRPV14 for 8 hours. After treatment, cells were washed with PBS and cultured with fresh media, with half-media exchanges every other day. At 0, 4, 12 hours, and 1, 5, 10, 15 or 20 days after treatment, cells were challenged with HIV-1$_{ADA}$ at a MOI of 0.1 infectious particles per cell for 16 hours. After viral infection, the cells were cultured an additional 10 days with half-media exchanges every other day. Culture fluids were collected for measurement of RT activity. Cells were fixed with 4% PFA and expression of HIV-1p24 antigen was determined by immunocytochemistry.

Conversion of RPV into more hydrophobic and lipophilic MRPV and encasement into nMRPV nanoparticles significantly improved the potency and intracellular accumulation of the drug compared to nanoformulated RPV (nRPV). The MRPV nanoformulations were easily taken up by human monocyte derived macrophages (MDM) with sustained drug release throughout the 10 day measurement period (FIGS. 2A and 2B). Drug uptake and retention paralleled antiretroviral efficacy measured in MDM (FIGS. 2C and 2D).

A single intramuscular administration of nMRPV at a dose of 45 mg/kg RPV-equivalents led to a marked sustained plasma and tissue RPV concentrations at or above the $EC_{90}$ for up to two months post injection compared to nRPV (FIGS. 3A and 3B). Importantly, nMRPV exhibited enhanced tissue RPV levels for up to two months when compared against nRPV, demonstrating that nanoformulated MRPV significantly improves drug accumulation into tissues for sustained release.

Nanoparticles comprising MRPV14 and P407 were also synthesized. A single intramuscular administration of nMRPV14 into BALB/c mice at a dose of 100 mg/kg RPV-equivalents led to a marked sustained plasma RPV concentration at or above the $EC_{90}$ for months post injection compared to nRPV (FIG. 4A). nMRPV14 also exhibited enhanced tissue RPV levels at two months when compared against nanoformulations of RPV, demonstrating that nanoformulated MRPV significantly improves drug accumulation into tissues for sustained release (FIG. 4B).

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound represented by formula:

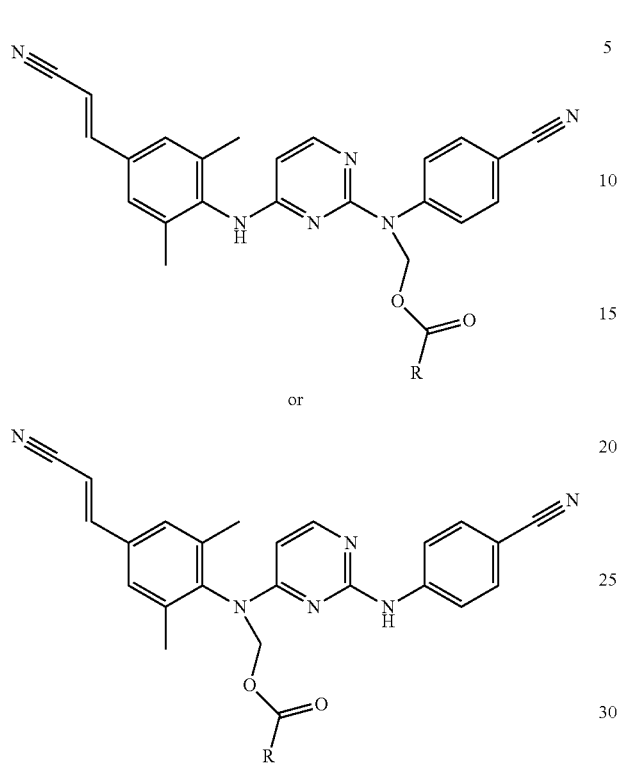

or a pharmaceutically acceptable salt thereof, wherein R is a C4-C24 unsaturated or saturated aliphatic group, optionally substituted with at least one heteroatom.

2. The compound of claim 1, wherein R is an alkyl chain of a fatty acid.

3. The compound of claim 1, wherein said compound is selected from the group consisting of:

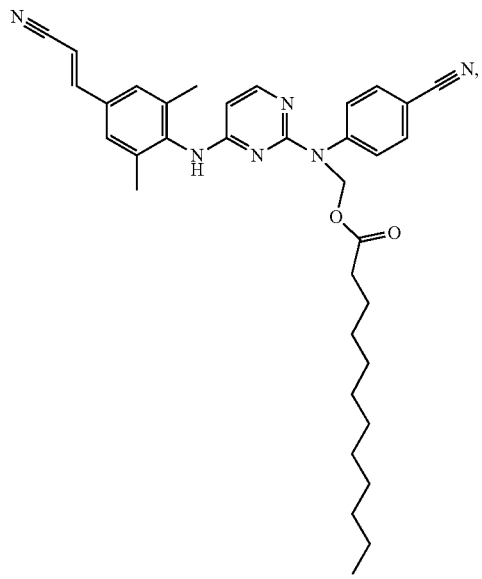

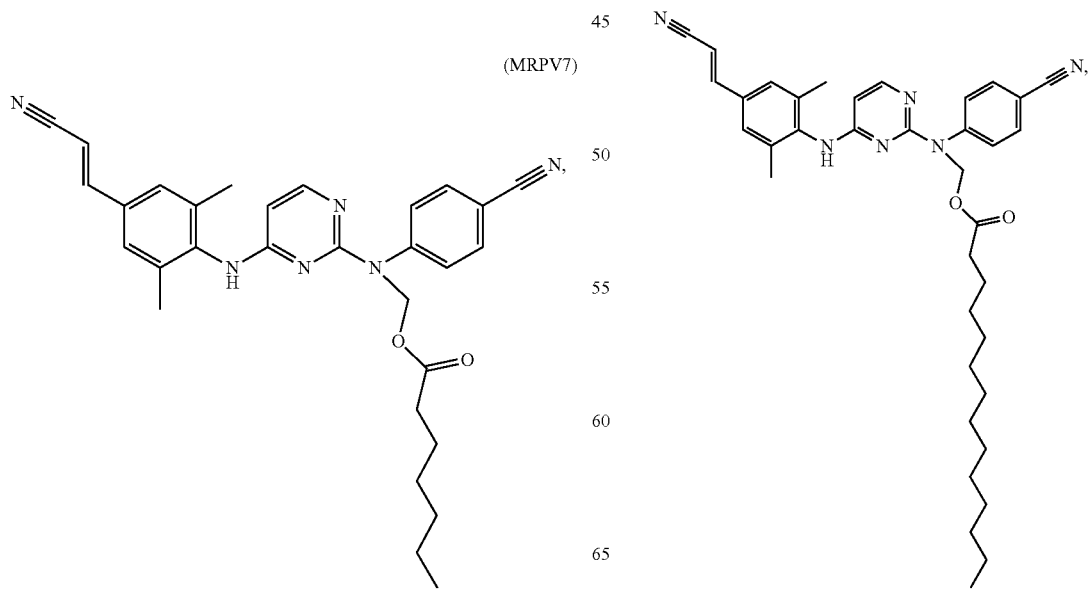

-continued

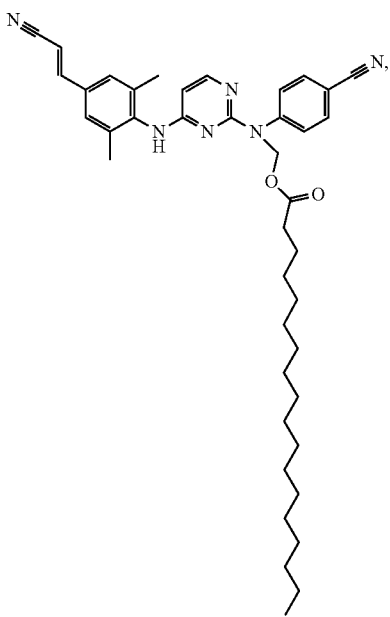

(MRPV18)

and pharmaceutically acceptable salts thereof.

4. A nanoparticle comprising at least one compound of claim 1, or a pharmaceutically acceptable salt thereof, and at least one polymer or surfactant.

5. The nanoparticle of claim 4, wherein said compound is crystalline.

6. The nanoparticle of claim 4, wherein said polymer or surfactant is an amphiphilic block copolymer.

7. The nanoparticle of claim 6, wherein said amphiphilic block copolymer comprises at least one block if poly(oxyethylene) and at least one block of poly(oxypropylene).

8. The nanoparticle of claim 6, wherein the polymer or surfactant is P407.

9. The nanoparticle of claim 4, wherein said nanoparticle further comprises a polymer or surfactant linked to at least one targeting ligand.

10. The nanoparticle of claim 4, wherein the diameter of the nanoparticle is about 100 nm to 1 μm.

11. A composition comprising at least one nanoparticle of claim 4 and at least one pharmaceutically acceptable carrier.

12. A pharmaceutical composition comprising at least one compound of claim 1, or a pharmaceutically acceptable salt thereof, and at least one pharmaceutically acceptable carrier.

13. A method for treating an HIV infection in a subject in need thereof, said method comprising administering to said subject an effective amount of a compound of claim 1, or a pharmaceutically acceptable salt thereof.

* * * * *